US011185520B2

(12) United States Patent
Laruelle et al.

(10) Patent No.: US 11,185,520 B2
(45) Date of Patent: Nov. 30, 2021

(54) COMPOSITION COMPRISING AT LEAST ONE WATER-SOLUBLE PHARMACEUTICALLY ACCEPTABLE SALT OF ELAFIBRANOR HAVING IMPROVED INTESTINAL ABSORPTION

(71) Applicant: NASHPHARM, Villeneuve Loubet (FR)

(72) Inventors: Claude Laruelle, Vlleneuve Loubet (FR); Ludovic Bonnafous, Mouans Sartoux (FR)

(73) Assignee: NASHPHARM, Viileneuve Loubet (FR)

( * ) Notice: Subject to any disclaimer, the term of this patent is extended or adjusted under 35 U.S.C. 154(b) by 0 days.

(21) Appl. No.: 16/338,219

(22) PCT Filed: Sep. 28, 2017

(86) PCT No.: PCT/EP2017/074701
§ 371 (c)(1),
(2) Date: May 8, 2019

(87) PCT Pub. No.: WO2018/060372
PCT Pub. Date: Apr. 5, 2018

(65) Prior Publication Data
US 2019/0274982 A1 Sep. 12, 2019

(30) Foreign Application Priority Data

Sep. 30, 2016 (FR) ...................................... 1659438

(51) Int. Cl.
| | | |
|---|---|---|
| *A61K 31/192* | (2006.01) | |
| *A61P 1/16* | (2006.01) | |
| *A61K 9/00* | (2006.01) | |
| *A61K 9/14* | (2006.01) | |
| *A61K 47/10* | (2017.01) | |

(52) U.S. Cl.
CPC .......... *A61K 31/192* (2013.01); *A61K 9/0019* (2013.01); *A61K 9/14* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 2005/0148594 A1 | 7/2005 | Cink et al. | |
| 2012/0192861 A1* | 8/2012 | Surber ................. | A61K 9/0078 128/200.16 |
| 2012/0252725 A1* | 10/2012 | Darteil ................. | A61K 31/155 514/6.5 |

FOREIGN PATENT DOCUMENTS

| | | |
|---|---|---|
| EP | 1525177 A1 | 4/2005 |
| EP | 2641596 A1 | 9/2013 |
| WO | 2004005233 A1 | 1/2004 |
| WO | 2016154258 A1 | 9/2016 |

OTHER PUBLICATIONS

Piyush, Patel et al., "Comparison of efficacy and safety of choline fenofibrate (fenofibric acid) to micronized renofibrate in patients of mixed dyslipidemia: A randomized, open-label, multicenter clinical trial in Indian population," Indian Journal of Endocrinology and Metabolism, vol. 20, No. 1, pp. 67-71, Jan. 1, 2016.
International Search Report from corresponding International Application No. PCT/EP20171074701, dated Nov. 20, 2017, pp. 1-4, European Patent Office, Rijswijk, The Netherlands.

* cited by examiner

*Primary Examiner* — Robert T. Crow
*Assistant Examiner* — John P Nguyen
(74) *Attorney, Agent, or Firm* — Hauptman Ham, LLP

(57) ABSTRACT

A composition comprising, as an active principle, a pharmaceutically acceptable salt of elafibranor, characterised in that the pharmaceutically acceptable salt of elafibranor is chosen from at least a salt of choline, of ethanolamine, or of diethanolamine, or of L-lysine, or of piperazine, or of calcium, or of tromethamine. More particularly, one or more embodiments relate to the use of elafibranor salts with a view to improving stability and solubility compared with elafibranor in the basic form thereof. These salts make it possible to establish pharmaceutical formulations in various advantageous forms as intravenous injections or formulations by enteral route having quicker and less variable absorption and consequently better bioavailability.

17 Claims, 12 Drawing Sheets

Figure 1 (formula I)

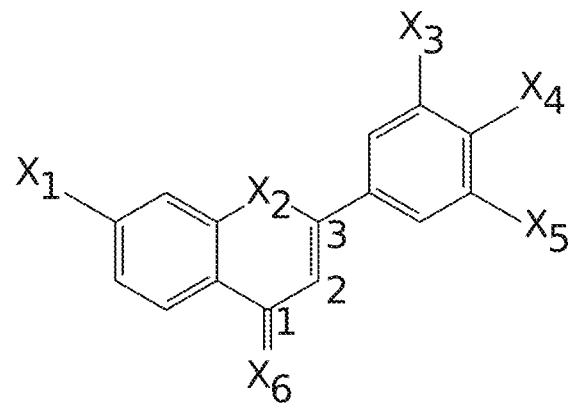
Figure 3: (formula II)
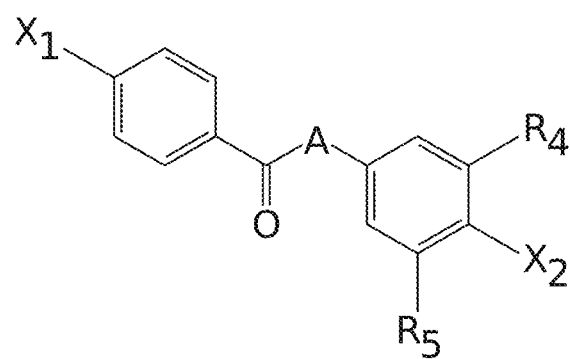
Figure 4: (formula III)

LCMS ANALYTICAL CONDITIONS:

Column: ACQUITY UPLC® BEH C18 1.7μm

Solvent A: Water + 0.1% formic acid + 0.5% ammonia
Solvent B: MeCN + 0.1% formic acid
Gradient % A:
- - 95% to 5% in 1 minute 3 seconds
- - Plateau at 5% for 45 seconds
- - Return to 95% in 6 seconds
- - Plateau at 95% for 54 seconds Flow rate: 0.8 millilitres/min Wavelength: Scanning from 210 nm to 400 nm UV spectrum

COMPOSITION COMPRISING AT LEAST ONE WATER-SOLUBLE PHARMACEUTICALLY ACCEPTABLE SALT OF ELAFIBRANOR HAVING IMPROVED INTESTINAL ABSORPTION

TECHNICAL FIELD

The present invention relates to drugs derived from elafibranor.

The invention relates in particular to a composition soluble in an aqueous medium having improved intestinal absorption. It relates to the use of pharmaceutically acceptable salts of elafibranor (GFT505), which can be used in pharmaceutical compositions.

The invention relates more particularly to the use of elafibranor salts with a view to improving stability and solubility compared with elafibranor in its basic form. These salts make it possible to establish pharmaceutical formulations in various advantageous forms such as intravenous injections or formulations for enteral route having quicker and less variable absorption and consequently better bioavailability.

PRIOR ART

Elafibranor, also cited under its code name GFT505, is an experimental module from the company Genfit developed initially for treating metabolic illnesses including diabetes, insulin resistance and dyslipidaemia. Its current therapeutic target is the treatment of liver disease, in particular non-alcoholic steatohepatitis (NASH).

Its chemical name is 2-[2,6 dimethyl-4-[3-[4-(methylthio)phenyl]-3-oxo-1(E)-propenyl]phenoxyl]-2-methylpropanoic acid, of chemical formula $C_{22}H_{24}O_4S$ and with a molecular weight of 384.489 g/mol. Its chemical structure of formula I is given in FIG. 1.

According to the Genfit patent EP 1525177 B1, which describes the use and preparation of molecules in the 1,3-diphenylprop-2-en-1-one family, elafibranor, referred to as compound 29 in this document, is identified by an NMR (1H DMSO) spectrum with the following characteristics (6 ppm): 1.39 (s, 6H), 2.22 (s, 6H), 2.57 (s, 3H), 7.40 (d, J=8.55 Hz, 2H), 7.57 (s, 2H), 7.62 (d, J=15.5 Hz, 1H), 7.83 (d, J=15.5 Hz, 1H), 8.10 (d, J=8.55 Hz, 2H), 12.97 (s, 1H) SM (ES-MS): 383.3 (M−1).

There are no other publically available documents providing more ample information on the physicochemical identification of this molecule, which comprises the same phenoxylated propanoic acid group as the molecules in the fibrate family (FIG. 2).

The molecules belonging to the fibrate family are known for their low solubility in water, whether in the ester form or the carboxylic acid form as is elafibranor (GFT505). In addition, appreciable variabilities in the pharmacokinetics of these molecules should be noted, such as for example for phenofibrate, the pharmaceutical formulations of which have been the subject of regular contributions from galenic innovation work to remedy these drawbacks and thus to improve bioavailability.

The other information available on elafibranor concerns mainly the preclinical, clinical and toxicological properties of this molecule. Elafibranor is in fact identified therein as being a coactivator of the nuclear receptors PPARα/δ. All clinical trials have shown a very good tolerance profile for this molecule, reinforced in particular by high-dose toxicological studies in animals including carcinogenicity studies.

Elafibranor (GFT05) also has beneficial effects on non-alcoholic steatohepatitis NASH with an improvement in the biochemical markers of hepatic malfunctioning, in particular the hepatic enzymes: ALAT, ASAT, γGT, and ALP7.

Currently there are no thorough descriptions of the physical and chemical data of elafibranor, whether it be the chemical molecule alone or as an active molecule in a pharmaceutical composition. No physiologically acceptable salt is described in patents or scientific publications.

Elafibranor (GFT505) has been described since 2003 in several patents of the company Genfit, which cover any therapeutic application and, since 2009, on a novel specific therapeutic application, in particular for treating non-alcoholic steatohepatitis NASH.

The patents EP1525177 and U.S. Pat. No. 7,943,661 relate to a novel family of derivatives of chalcones. They describe the method for preparing and using substituted derivatives of 1,3-diphenylprop-2-en-1-one of formula II below (FIG. 3), of which the elafibranor molecule forms part (compound 29 described in the description, claim 25), for any therapeutic application, without limitation to a precise illness.

The second family of patents EP2504005, U.S. Pat. Nos. 8,772,342 and 9,221,751 relate to compounds for use in a method for treating a liver disease chosen from the group consisting of hepatic fibrosis or hepatic steatosis.

In particular, claim 7 relates to the elafibranor molecule for use in the treatment of hepatic fibrosis or hepatic steatosis. Claims 9 and 10 relate to a pharmaceutical composition comprising a compound of the following formula III (FIG. 4) in a method for treating a liver disease chosen from the group consisting of hepatic fibrosis or hepatic steatosis.

The patent EP2504005B1 was the subject of a divisional application EP2641596A1 concerning the compounds claimed in the patent EP2504005B1, but used this time solely in the specific context of the illnesses: cirrhosis of the liver, alcohol-related illnesses and immune mediated liver diseases.

Other patents dealing with elafibranor should be noted. The U.S. Pat. No. 7,566,737B relates to a pharmaceutical composition comprising an association between a substituted derivative of 1,3-diphenylprop-2-en-1-one of formula II, including the elafibranor molecule, and another ingredient having therapeutic activity.

The U.S. Pat. No. 8,895,619 B relates to a method for treating hepatic fibrosis by the administration of the elafibranor molecule (claims 1-7, 10-11) and in particular for treating cirrhosis (claims 8-9).

The application US2016/0051501 relates to a method for treating a viral or alcohol-related or immune liver illness by a compound of formula III.

Elafibranor is not cited in other patents. Only results of studies appear in several articles, the first of which were published in 2007 (Fruchart, Am J Cardiol 2007; 100 [suppl]:41N-46N; in 2013: Fruchart Cardiovascular Diabetology 2013, 12:82).

The posting "The hepatic and extra-hepatic profile of resolution of steatohepatitis induced by GFT-505 (elafibranor)" by Sanyal A J et al., deals with the results of a phase 2b study (Golden505) proposing a daily dose of 80 or 120 mg of elafibranor administered to 270 NASH patients (3 groups including diabetics and non-diabetics). There is no information about the pharmaceutical composition of the capsules dosed at 40 mg used for the study or on the physical and chemical characteristics of the elafibranor or the rationale concerning the administration before breakfast.

The pharmacokinetic parameters including metabolism are not publically available for elafibranor despite the phase 1 studies that have been carried out. In 2012, in the dose research study "*Comparative Bioavailability—Gender Effect—Single and Multiple Ascending Dose Safety and Pharmacokinetic Study of GFT505*", changes were made by Genfit in the formulations of elafibranor. A study of the relative bioavailability between new and old formulations was carried out, on a dose range of up to 300 mg. There is no publication of results or information that justify and support the reasons for this formulation work.

Elafibranor as described in the Genfit patents is put in particular galenic forms. In particular, elafibranor is not found in the form of intravenous injections or in formulations that are effected by enteral route.

Surprisingly, it has been found that the use of specific pharmaceutically acceptable salts of elafibranor improves the stability and solubility thereof, thus providing a new galenic form and better bioavailability.

BRIEF DESCRIPTION OF THE FIGURES

The aims, objects, features and advantages of the invention will emerge more clearly from the detailed description of an embodiment thereof that is illustrated by the following accompanying figures, in which:

FIG. 3: chemical formula derived from substituted 1,3-diphenylprop-2-en-1-one comprising elafibranor.

FIG. 4: general formula of a compound in the patent application EP2504005 comprising elafibranor.

DISCLOSURE OF THE INVENTION

Figure 1:
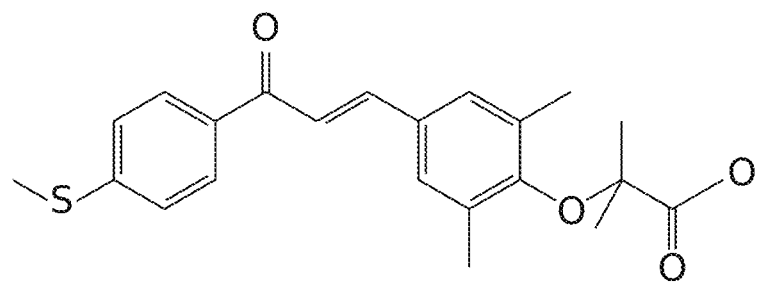
FIG. 1: chemical formula of elafibranor.

Before beginning a detailed review of embodiments of the invention, optional features that may optionally be used in association or alternatively are set out below.

The invention relates to a composition comprising as an active principle a pharmaceutically acceptable salt of elafibranor, characterised in that the pharmaceutically acceptable salt of elafibranor is chosen from at least one salt of choline, or of ethanol amine, or of diethanolamine, or of L-lysine or of piperazine, or of calcium, or of tromethamine.

Advantageously, the pharmaceutically acceptable salt is the choline salt.

Advantageously, the composition is in a form suitable for enteral administration.

Advantageously, the composition is in a form suitable for parenteral administration.

The parenteral administration modes afford rapid absorption and optimum bioavailability.

Advantageously, the composition is in a form suitable for intravenous administration.

Advantageously, the elafibranor salt is micronised or has an amorphous structure.

Advantageously, the elafibranor salt is in the form of a powder for soluble injectable preparation.

Advantageously, the composition is in a form suitable for subcutaneous administration.

Advantageously, the composition comprises at least one excipient chosen from binders, disintegrating agents, diluents, lubricants, surfactants, buffers, flow agents, dyes, flavourings, sweeteners, solvents or preservatives.

Advantageously, the composition comprises more than 50% of particles with a size less than or equal to 10 µm and all the particles with a size less than 20 µm.

Advantageously, the pharmaceutically acceptable elafibranor salt is configured to have solubility at least equal to 10 mg/ml in a 0.9% NaCl physiological medium.

Advantageously, the elafibranor salt is configured to have a dissolution profile in a simulated FaSSIF and FeSSIF medium greater than 90% after 30 minutes.

Advantageously, the pharmaceutically acceptable elafibranor salt (GFT505) is configured so as to be photostable.

Photostable means the capacity to be less sensitive to light.

Advantageously, the composition is intended to be used in the treatment of liver diseases.

Advantageously, the liver disease consists of non-alcoholic hepatic steatosis (NAFLD).

Advantageously, the composition is intended to be used in the treatment of liver diseases, characterised in that the liver disease consists of non-alcoholic steatohepatitis (NASH).

Advantageously, the liver disease consists of hepatic fibrosis.

Advantageously, the liver disease consists of cirrhosis.

Advantageously, the liver disease consists of hepatic autoimmune illnesses.

Advantageously, the administration method consists of oral administration.

Advantageously, the administration method consists of subcutaneous administration.

Advantageously, the medicinal form consists of a powder for oral suspension.

The pharmaceutically acceptable elafibranor salt has the advantage of having better solubility in water compared with the basic form.

Advantageously, the medicinal form consists of an injectable solution, a tablet, a dispersible tablet, an orodispersible tablet, a capsule, a soluble tablet, a freeze-dried product, an effervescent tablet, a tablet for chewing, a slow-release tablet or a sachet.

Advantageously, the dissolution profile in simulated FaSSIF and FeSSIF media of the pharmaceutically acceptable elafibranor salt has a dissolution percentage greater than 90% after 30 minutes.

Advantageously, the medicinal form comprises particles of elafibranor, with at least 50% of the particles being of sizes less than 10 µm.

Advantageously, the composition comprises at least one physiologically acceptable excipient, in particular at least one from binders, disintegrating agents, diluents, lubricants, surfactants, buffers, flow agents, dyes, flavourings, sweeteners, solvents or preservatives.

The invention relates to a use of a composition comprising as active principle at least one pharmaceutically acceptable salt of elafibranor (GFT505) for obtaining a drug intended for use in the treatment or prevention of illnesses, in particular hepatopathy including, non-exhaustively, non-alcoholic hepatic steatosis (NAFLD), non-alcoholic steatohepatitis (NASH), liver fibrosis, cirrhosis and hepatic autoimmune illnesses.

In another aspect, the invention relates to the preparation of pharmaceutically acceptable salts of elafibranor (GFT505) demonstrating more advantageous physical and chemical properties than the basic form of elafibranor, in particular with regard to solubility and/or stability.

DETAILED DESCRIPTION

The present invention relates to the use of a pharmaceutically acceptable salt of elafibranor and any of the derivatives thereof, in one of its crystalline forms, optionally polymorphous, or according to an amorphous crystallised structure, in the preparation of a drug for treating or preventing illnesses, in particular liver diseases such as non-alcoholic hepatic steatoses (NASH and NAFLD), fibroses, cirrhoses or cancer, or autoimmune illnesses.

The invention also relates to the use of a pharmaceutically acceptable salt of 2-[2,6 dimethyl-4-[3-[4-(methylthio)phenyl]-3-oxo-1 (E)-propenyl]phenoxyl]-2-methylpropanoic acid, of chemical formula $C_{22}H_{24}O_4S$ (FIG. 1), able to be used in a pharmaceutical composition for preventing or treating diseases, in particular liver diseases.

"Pharmaceutically acceptable salt" means, by way of example and non-exhaustively, physiological salts of: choline, ethanol amine, diethanolamine, L-lysine, piperazine, calcium and tromethamine.

The pharmaceutically acceptable salt is for example in one of the crystalline forms thereof, optionally polymorphous, or according to an amorphous crystalline structure.

The elafibranor salt is also referred to as elafibranorate salt.

The pharmaceutical composition according to the invention can be administered enterally, parenterally, topically or subcutaneously. According to one administration method, the composition is administered enterally, such as, for example, a tablet, a capsule, a soft capsule, a freeze-dried product, a dispersible, orodispersible, effervescent or soluble tablet, an oral solution or a powder for oral suspension.

According to a preferred administration method, the composition is administered intravenously, subcutaneously, in the form of for example an injectable solution or a powder for injectable solution.

The formulations intended to be administered intravenously or orally advantageously contain a micronised elafibranor salt or one with an amorphous structure in order to optimise the aqueous solubility and enteric dissolution where applicable. The distribution of the particle size of the elafibranor salts that have a crystalline structure is characterised in that more than 50% of the particles are less than or equal to 10 μm, and all the particles have a size less than 20 μm.

The particles are measured by means of a Malvern laser granulometer or equivalent, and a validated wet method (wetting with a surfactant) is preferred.

One of the pharmaceutically preferred compositions of the invention is a powder for an injectable preparation that is soluble and stable under normal conditions of temperature and humidity, that is to say 25° C./60% RH (ICH conditions).

The following examples are given to illustrate the invention and in no way constitute a limitation thereof.

EXAMPLES

Example 1: Synthesis and Characterisation of Elafibranor (GFT505)

The applicant decided to prepare samples of elafibranor to assess the feasibility of the steps of synthesis of this molecule and to characterise the physical and chemical properties of the product obtained. The operating method is derived from the information described in the patent EP 1525177 B1 for synthesising compound 29. The steps are produced identically.

Experimental Protocol

The compound is synthesised from 1-[4-methylthiophenyl]-3-[3,5-dimethyl-tertiobutyloxycarbonyldimethylmethyloxyphenyl]prop-2-en-1-one.

Step 1: 1-[4-methylthiophenyl]-(E)-3-[3,5-dimethyl-4-hydroxyphenyl]prop-2-en-1-one (intermediate 1)

4-methylacetophenone (20 g, 0.12 mol, 1 eq) and 3,5-dimethyl-4-hydroxybenzaldehyde (18 g, 0.12 mol, 1 eq) are solubilised in 300 ml of 4N HCl in dioxane. The reaction medium is stirred for 30 hours and then the solvents are evaporated. Purification by hot recrystallisation in 70 ml of isopropanol and 12 ml of water: 30 g (yellow solid, yield: 92%).

Raw formula: $C_{18}H_{18}O_2S$

ESI-MS m/z=299.18 [M+H]+

1H NMR DMSO-d6 δ ppm: 2.18 (s, 6H), 2.53 (s, 3H), 7.36 (d, J=8.5 Hz, 2H), 7.47 (s, 2H), 7.57 (d, J=15.5 Hz, 1H), 7.69 (d, J=15.5 Hz, 1H), 8.05 (d, J=8.5 Hz, 2H), 8.93 (s, 1H)

Step 2: 1-[4-methylthiophenyl]-(E)-3-[3,5-dimethyl-4-tertiobutylcarbonyldimethylmethyloxyhenyl]prop-2-en-1-one (intermediate 2)

Caesium carbonate (87 g, 0.134 mol, 4 eq) and tetrabutylammonium iodide
(12 g, 0.033 mol, 0.5 eq) are added to an intermediate solution 1 (20 g, 0.067 mol, 1 eq) in 50 ml of a DMSO/water mixture (3/2). The reaction medium is stirred for 30 minutes at 80° C. and tert-butyl bromoisobutyrate (30 g, 0.134 mol, 2 eq) is added. Then 2 additions of 2 eq of tert-butyl bromoisobutyrate diluted to 50% in DMSO are each made at an interval of 1 hour. The reaction medium is stirred for 2 days at 80° C. The reaction medium is left to cool to ambient temperature and then 1.5 litres of water are added and the product is extracted with dichloromethane (4 times). The organic phase is dried on a phase-separation cartridge and evaporated dry. Purification on silica gel (cyclohexane/ethylacetate: 95/5 to 80/20): 18 g (orange solid, yield: 61%).

Raw formula: $C_{26}H_{32}O_4S$

ESI-MS m/z=441.33 [M+H]+

1H NMR DMSO-d6 δ ppm: 1.36 (s, 6H), 2.19 (s, 6H), 2.48 (broad peak, H2O+9H), 2.54 (s, 3H), 7.38 (d, J=8.4 Hz, 2H), 7.55 (s, 2H), 7.59 (d, J=15.6 Hz, 1H), 7.80 (d, J=15.6 Hz, 1H), 8.07 (d, J=8.4 Hz, 2H)

Step 3: 1-[4-methylthiophenyl]-(E)-3-[3,5-dimethyl-4-carboxydimethylmethyloxyhenyl]prop-2-en-1-one Intermediate 2 (25 g, 0.057 mol, 1 eq) is solubilised in 50 ml of dichloromethane, and 22 ml of trifluoroacetic acid (5 eq, 0.284 mol) is added gently. The reaction medium is stirred for 3.5 hours at ambient temperature and then the solvents are evaporated dry. Purification on silica gel (dichloromethane/methanol: 100/0→95/5); 13 g (yellow solid, yield 60%).

Raw formula: $C_{22}H_{24}O_4S$
ESI-MS m/z=385.25 [M+H]+
1H NMR DMSO-d6 δ ppm: 1.36 (s, 6H), 2.19 (s, 6H), 2.54 (s, 3H), 7.37 (d, J=8.6 Hz, 2H), 7.55 (s, 2H), 7.59 (d, J=15.6 Hz, 1H), 7.80 (d, J=15.6 Hz, 1H), 8.07 (d, J=8.6 Hz, 2H), 12.94 (s, 1H)

Figure 5:
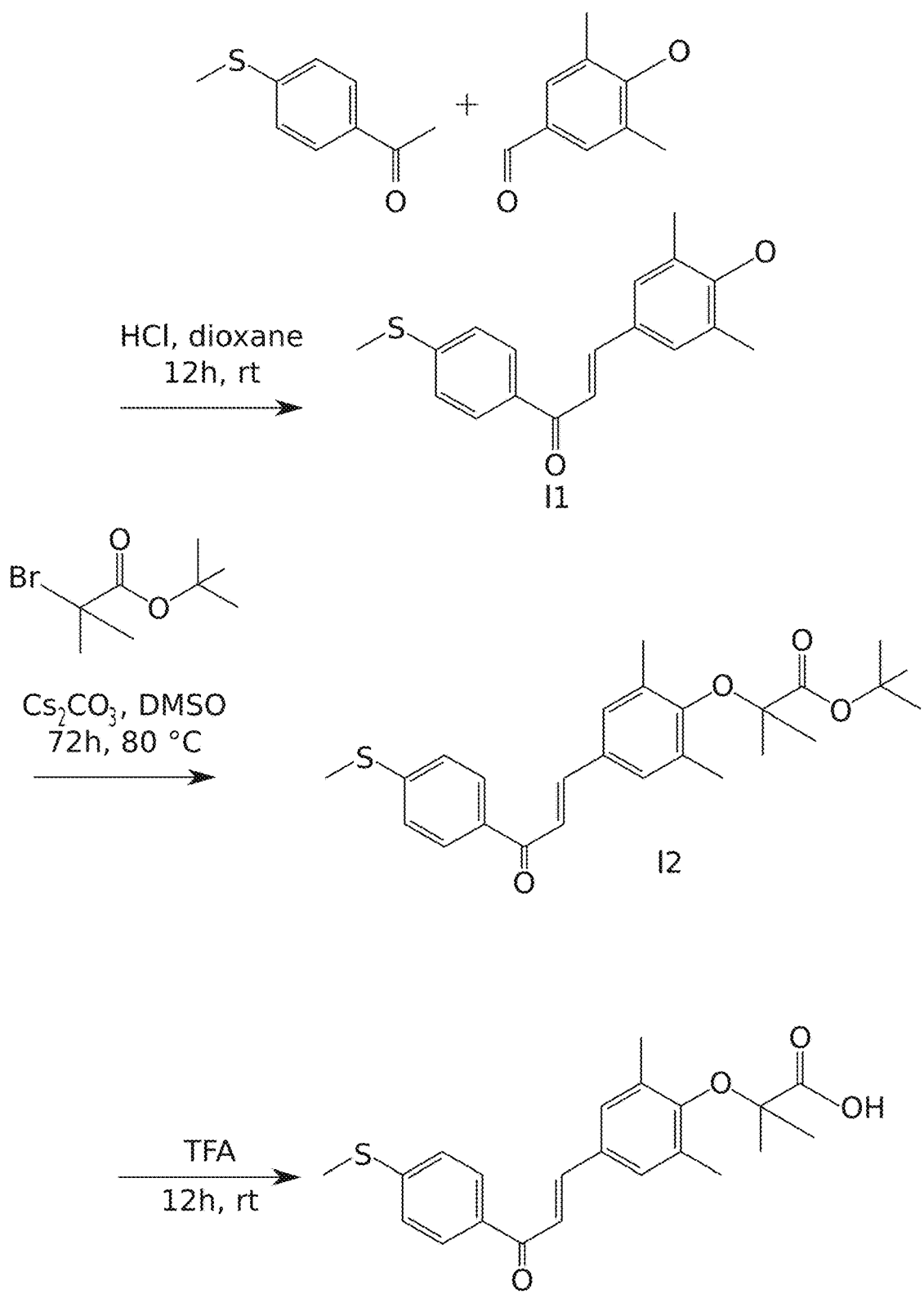
FIG. 5: synthesis diagram of elafibranor (GFT505)

The reaction diagram is given in FIG. 5.

Results

Figure 6A:
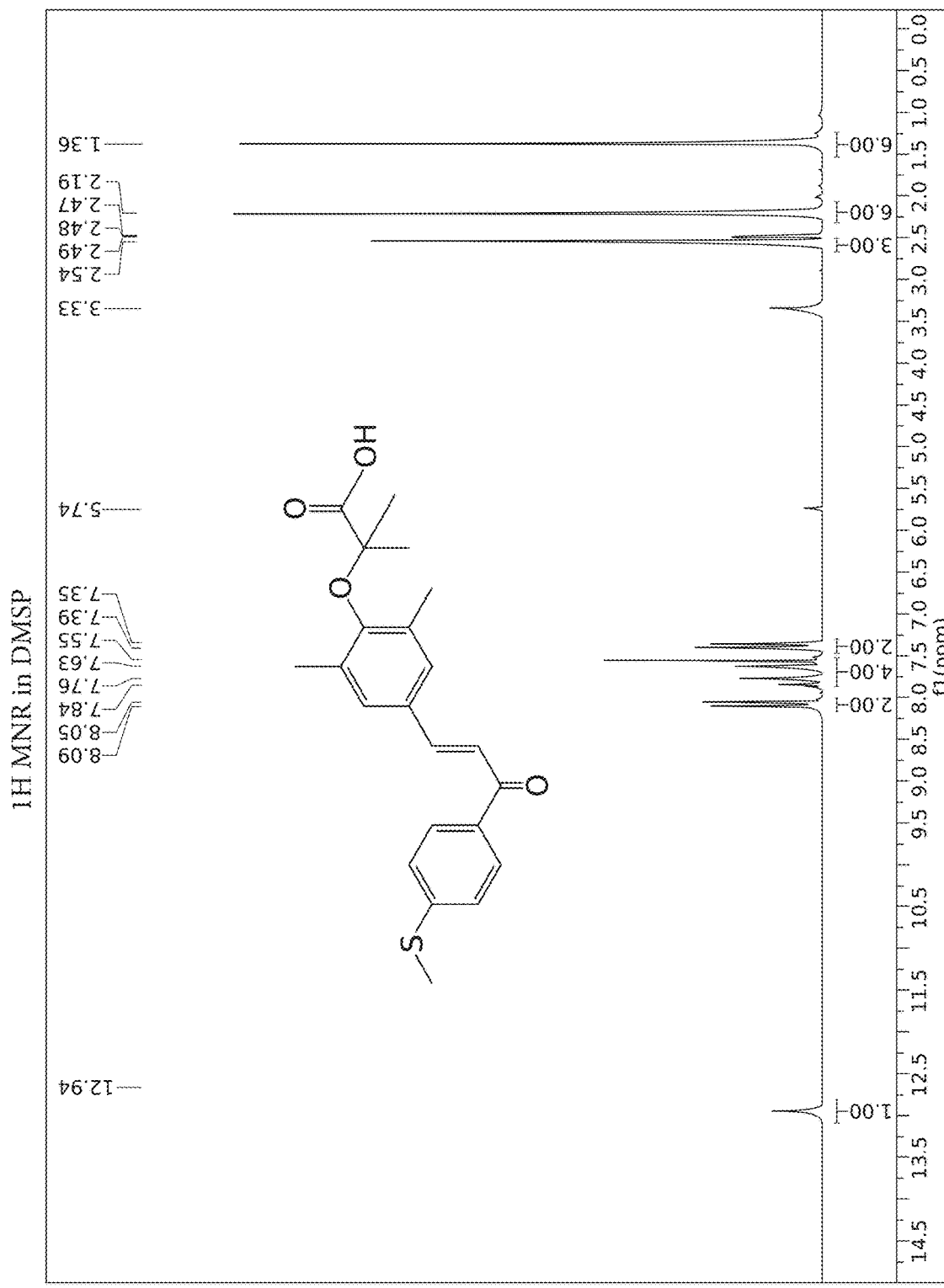
FIG. 6A: 1H NMR spectrum of elafibranor (GFT505)
Figure 6B:
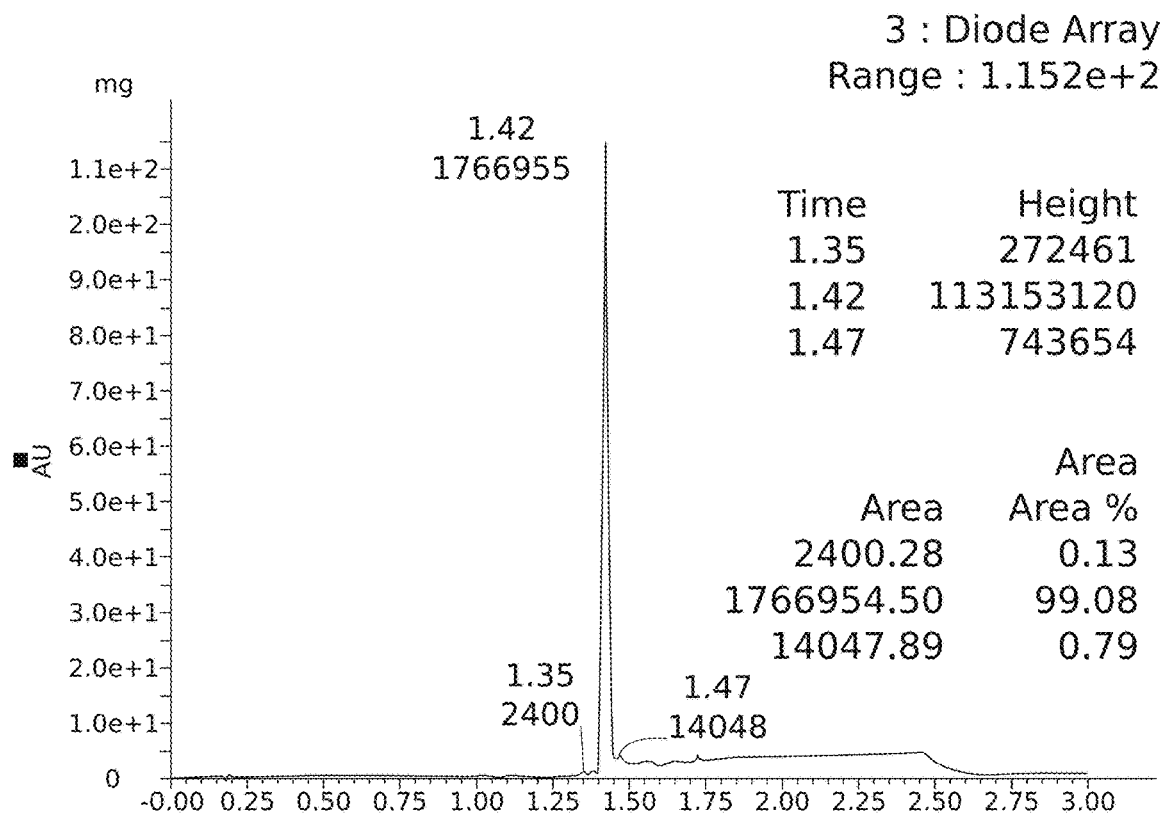
FIG. 6B: MS-MS spectrum of elafibranor (GFT505).
Figure 6C:
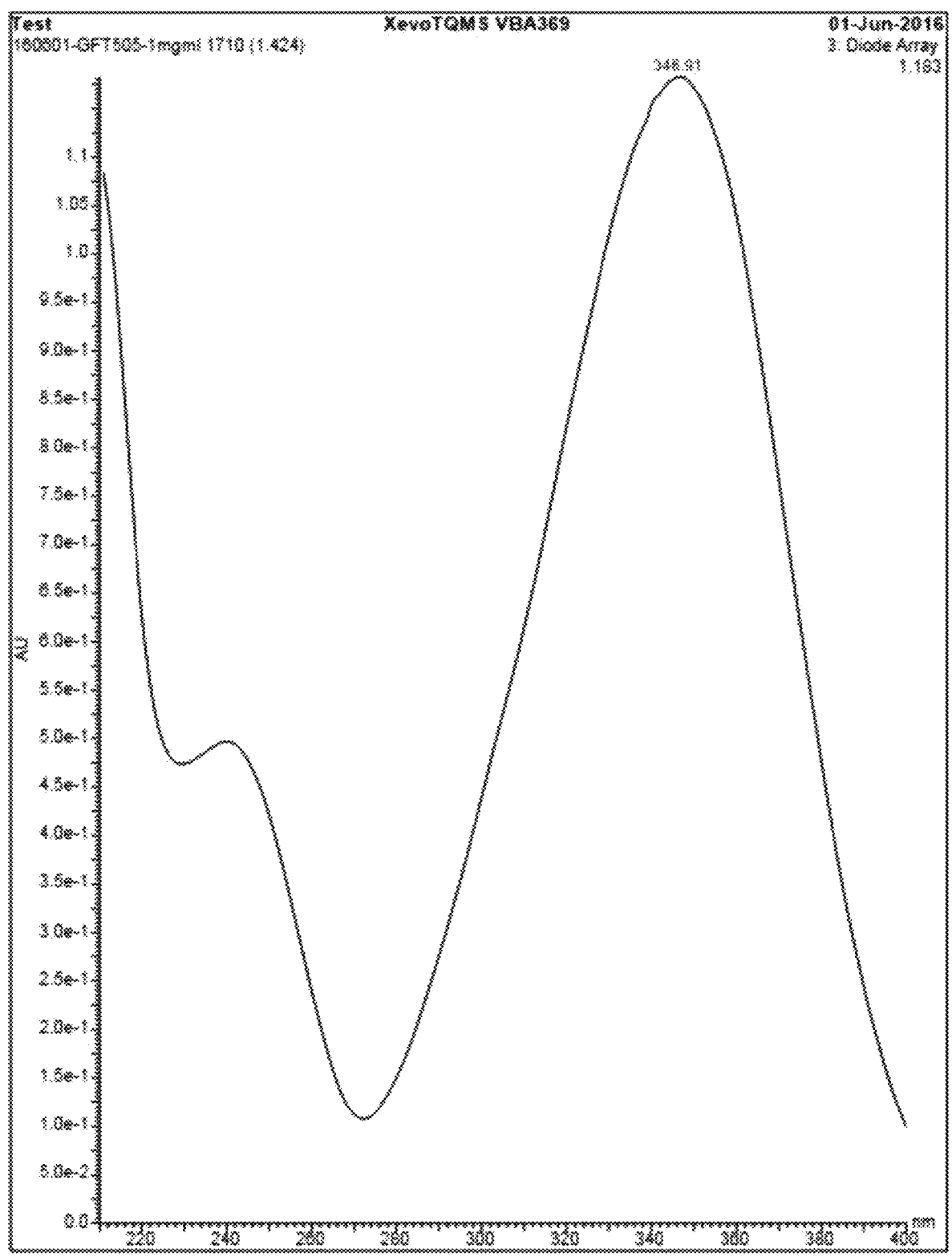
FIG. 6C: UV spectrum of elafibranor (GFT505)
Figure 6D:
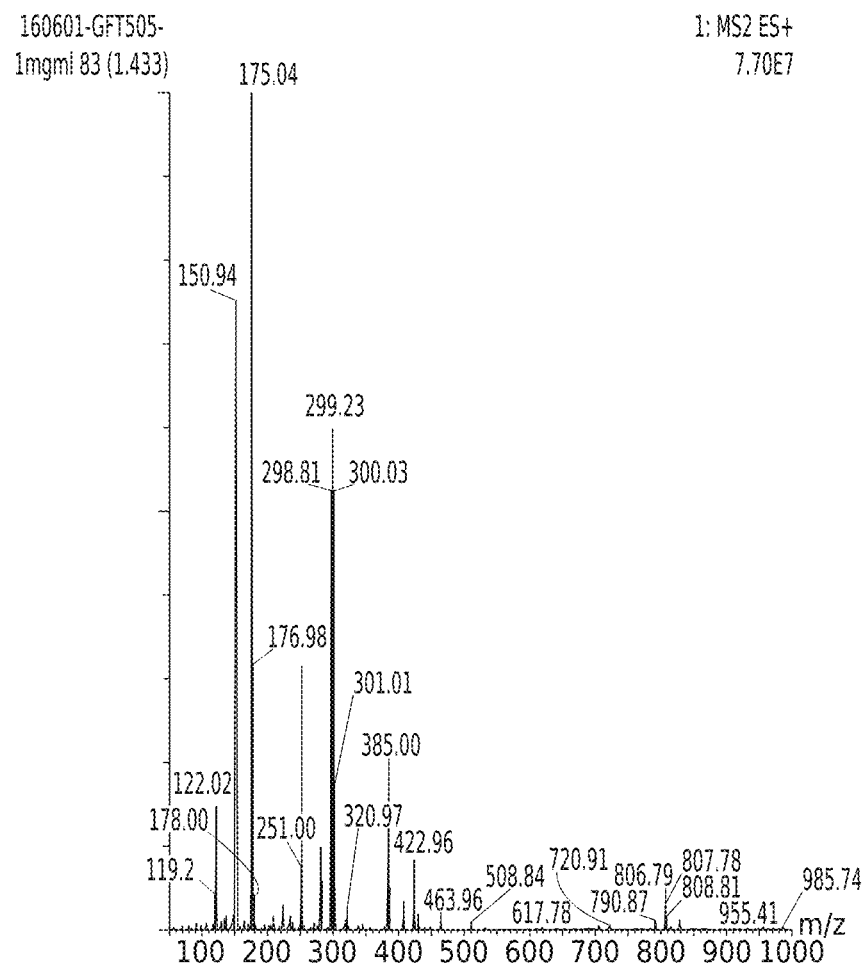
FIG. 6D: LC-MS spectrum of elafibranor (GFT505).
Figure 7A:
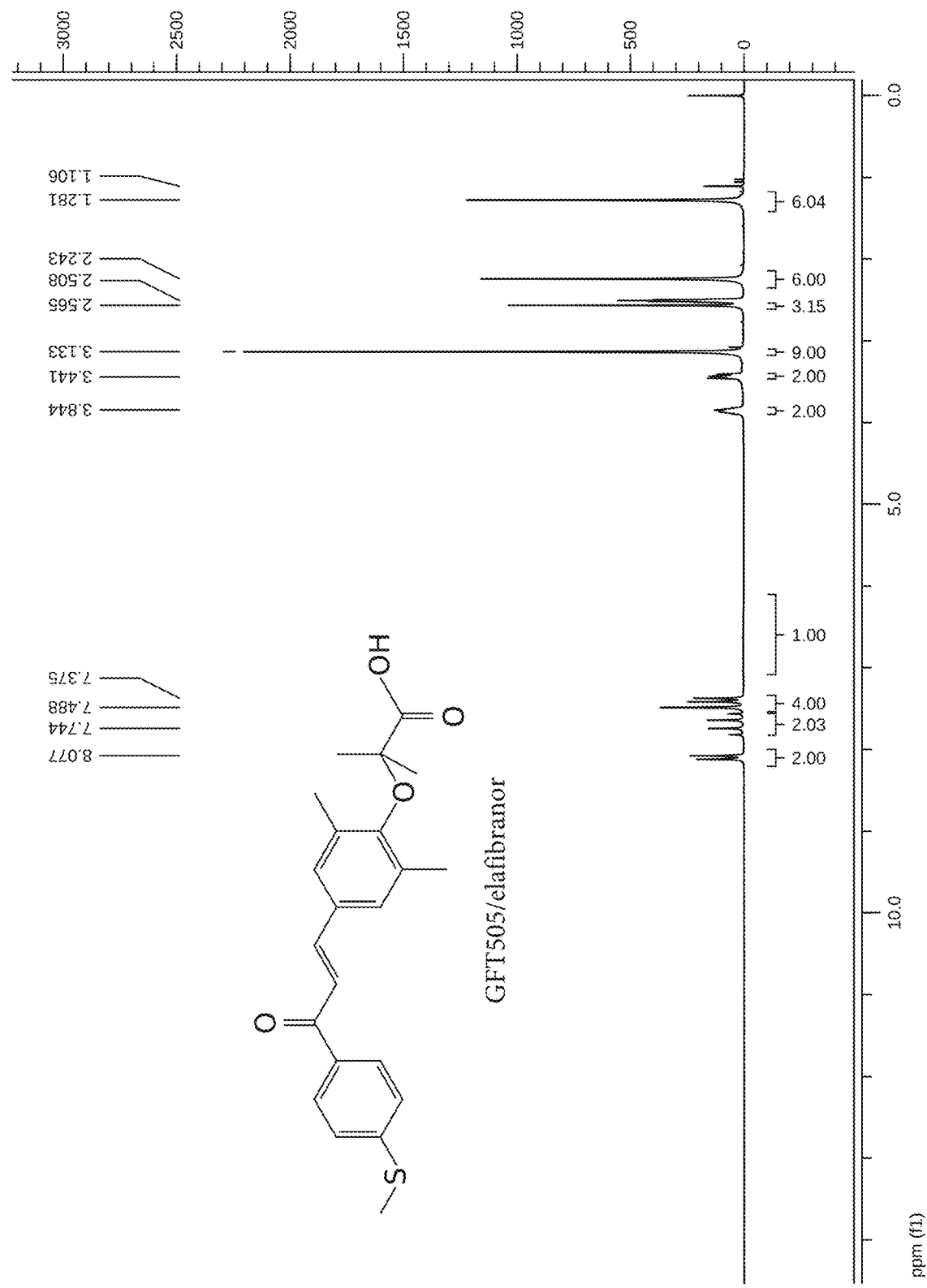
FIG. 7A: 1H NMR spectrum of the choline salt of elafibranor (GFT505)
Figure 7B:
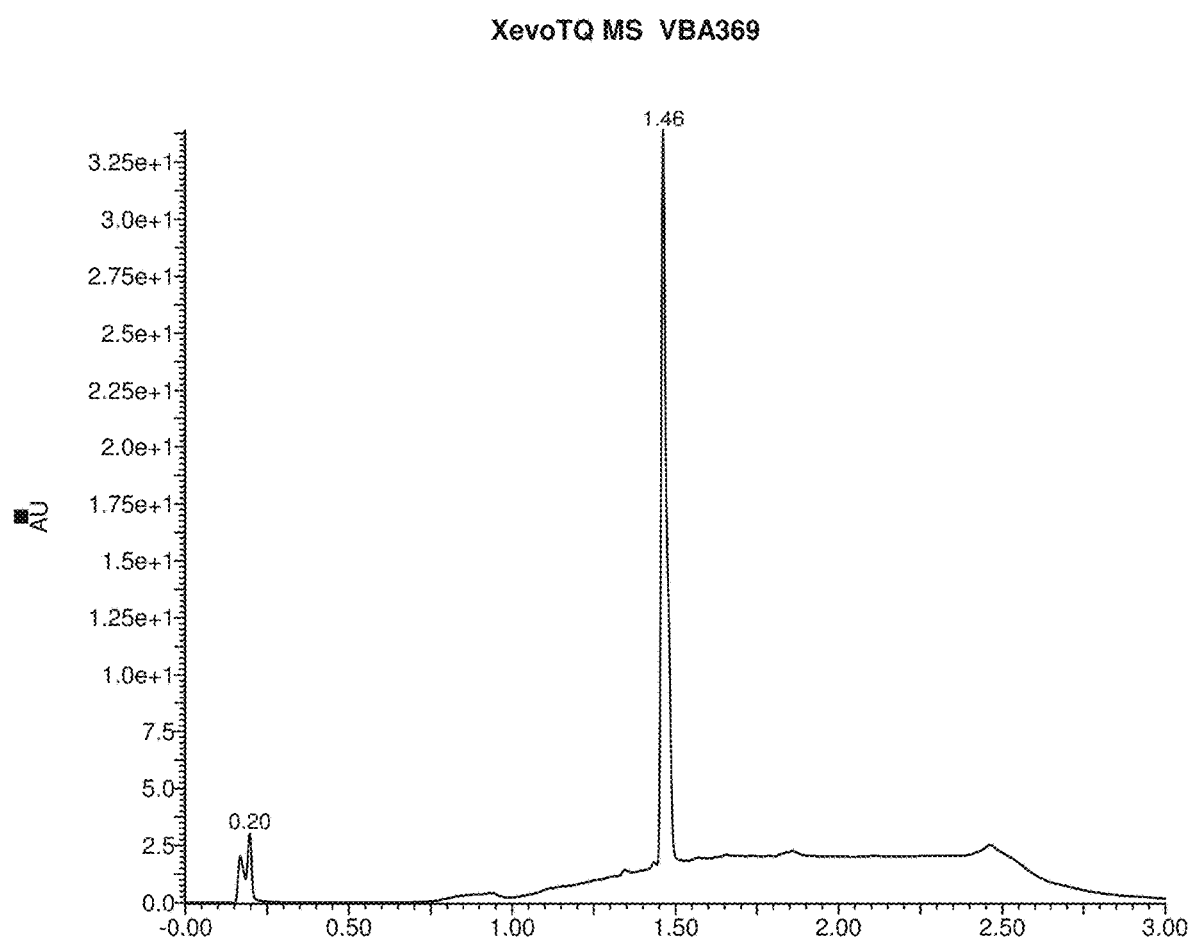
FIG. 7B: MS-MS spectrum of the choline salt of elafibranor.
Figure 7C:
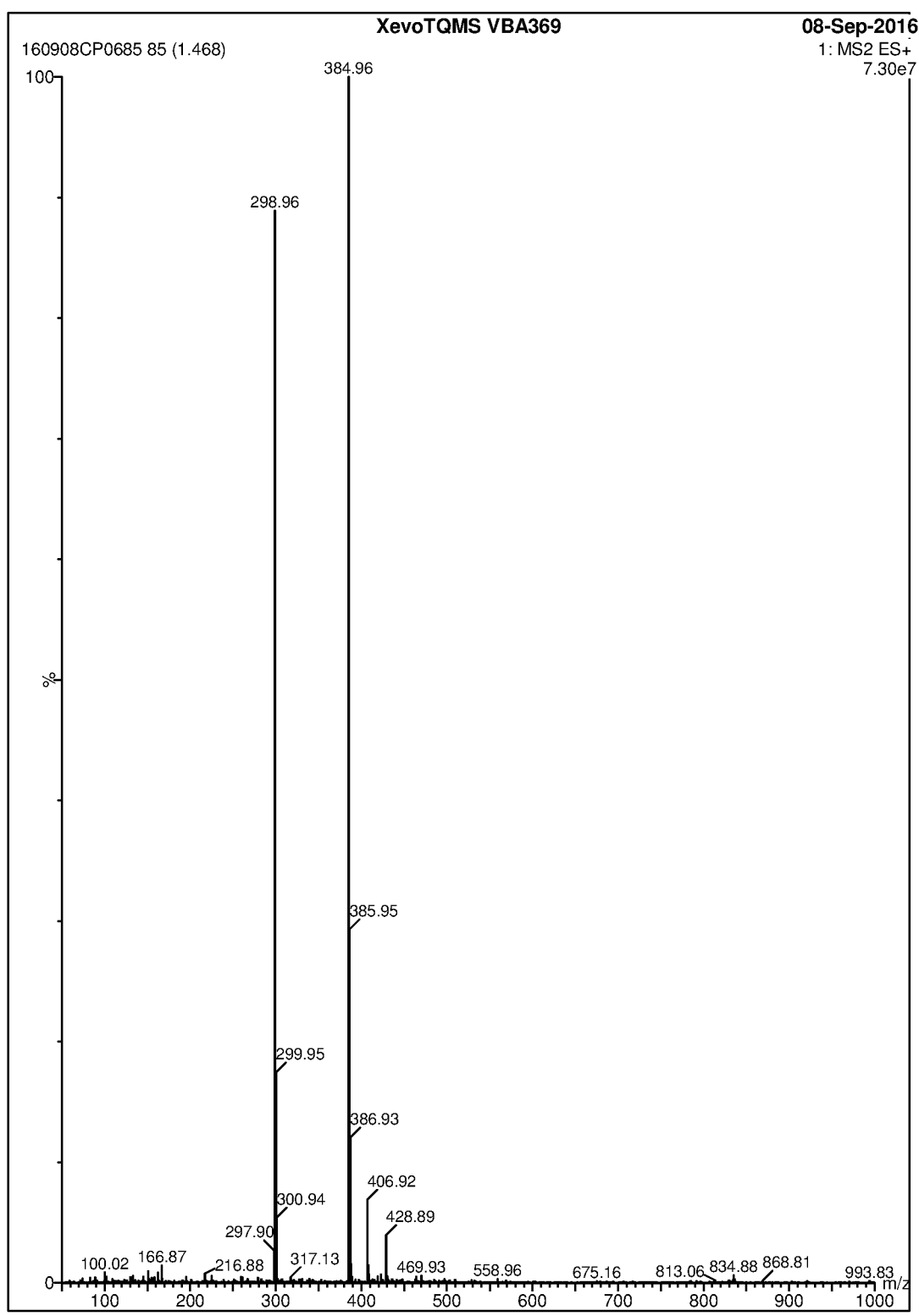
FIG. 7C: LC-MS spectrum of the choline salt of elafibranor.
Figure 7D:
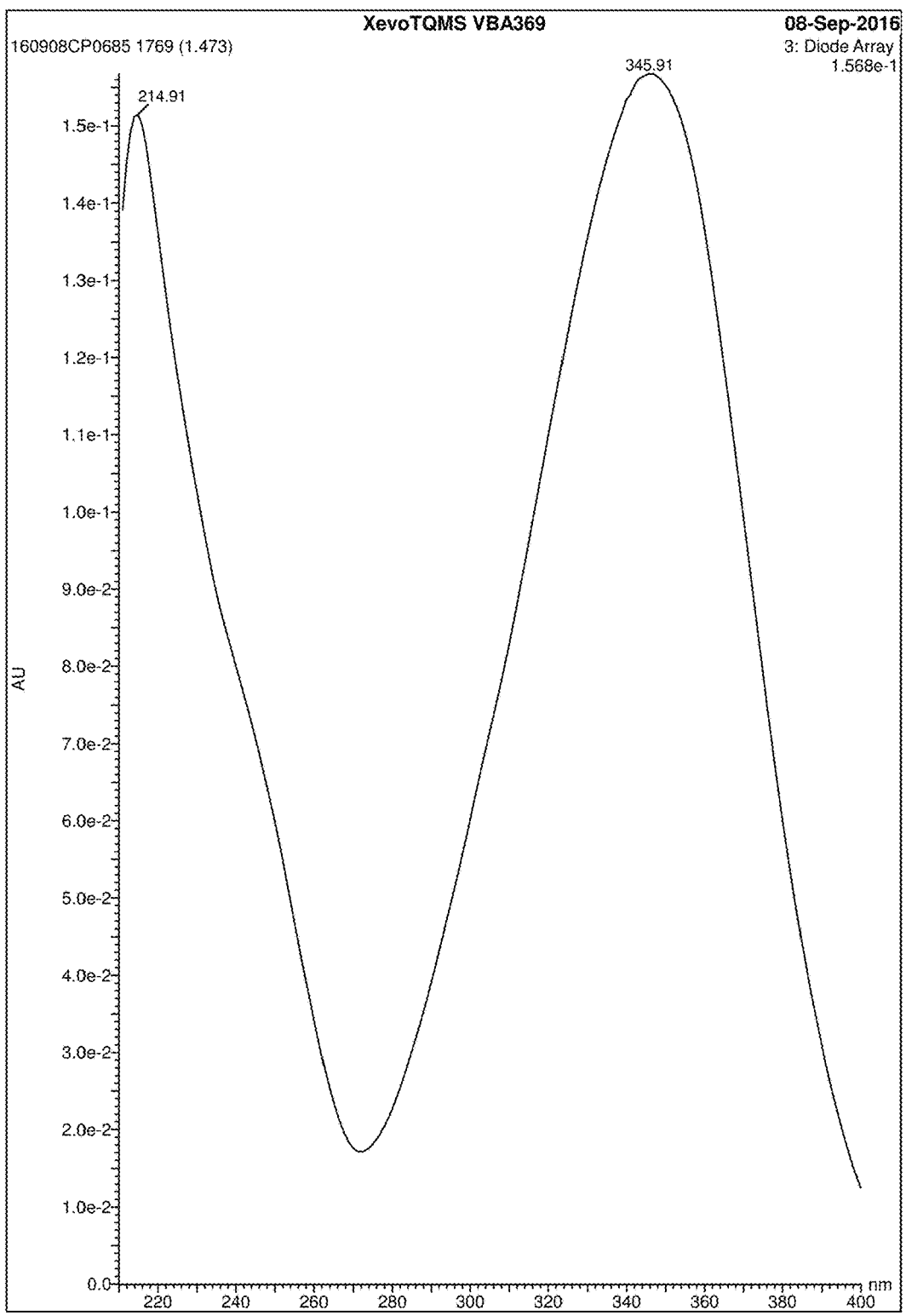
FIG. 7D: UV spectrum of the choline salt of elafibranor.

The analysis data of the 10.1 g of the batch obtained (EM0274L2) are summarised below:
- Molecular mass: 384.5 (exact mass: 384.1);
- 1H NMR spectrum: conforming to the structure, cf spectrum in FIG. 6A below.
- LCMS: TR=1.42 mn, m/z: 385.00=[M+H]+;
- Purity: >98% (1H NMR and LCMS);
- Melting point: 144-145° C.

The appearance of the product is an amorphous yellow solid powder. The product exhibits significant absorption in the near visible with an apex at approximately 347 nm.

The information is detailed in the following FIG. 6.

The product obtained is conforming in terms of chemical purity and demonstrates absorption in the near visible that requires that the chemical stability under light and phototoxicity must therefore be checked.

Example 2: Measurement of Solubility of Elafibranor (GFT505)

Figure 2:
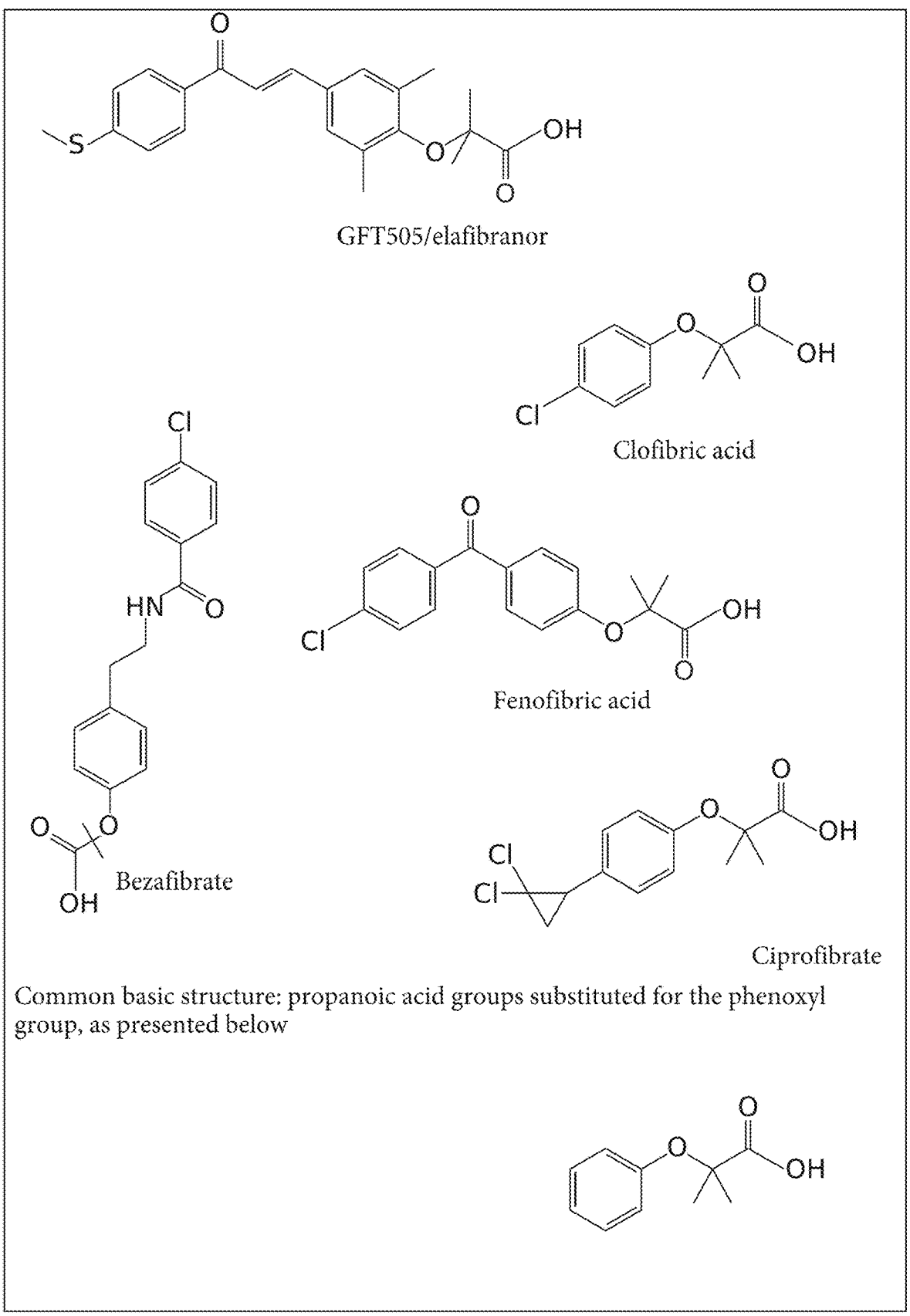
FIG. 2: chemical formula of fibrates and of the common chemical group of fibrates and elafibranor.

During an experiment carried out for the invention, it was shown that elafibranor (GFT505) had a chemical structure similar to the fibrate family (FIG. 2). Elafibranor being a carboxylic acid, the applicant chose to check the solubility in water of this molecule in order to rule on the feasibility of development of pharmaceutical compositions in accord with the expectations of patients, and that were more effective and tolerated by the patients.

Experimental Protocol

The thermodynamic solubility of the basic elafibranor is studied over a period of 24 hours and 72 hours in various aqueous buffers in the presence or not of surfactants. Batch number EM0274L2 is used for this work. The product is dissolved in the solvents indicated in table 1. After 24 hours and 72 hours of incubation at ambient temperature (22°–24° C.), the solutions are sampled and then filtered over 0.2 μm polycarbonate filters in flasks for LCMS analyses, and diluting once in DMSO before stirring for 2 minutes (vortex or sonification).

Results

The thermodynamic solubility results are given in table 1 below:

TABLE 1

Thermodynamic solubility of elafibranor in aqueous medium

| Solvents | Solubility after 24 hours | | Solubility after 72 hours | |
| --- | --- | --- | --- | --- |
| | μM | mg/ml | μM | mg/ml |
| Buffer pH 4.6 | 114 | 0.044 | 110 | 0.042 |
| Buffer pH 7.4 | 504 | 0.194 | 609 | 0.234 |
| Buffer pH 8.5 | 4419 | 1.701 | 4270 | 1.644 |
| Propylene glycol | 33520 | 12.905 | 35081 | 13.506 |
| Polyethylene glycol 400 | 39022 | 15.023 | 40971 | 15.774 |

The solubility of elafibranor is low in an aqueous medium. Increases as a function of the pH, changing from 114 to 4419 μm and from pH 4.6 to 8.5. The addition of cosolvent such as propylene glycol or PEG 400 significantly improves the solubility of the molecule.

Example 3: Preparation of Elafibranor Salts (GFT505)

One of the preferred administration methods is the parenteral method. In order to achieve this, the applicant prepared elafibranor salts for the purpose of improving the solubility of the elafibranor in order to be able to produce injectable solutions or powders for an injectable preparation.

Experimental Protocol

The salts are produced from a batch of previously synthesised elafibranor.

Choline Salt:

1 g of GFT505 (2.6 mmol) and 104 mg of NaOH (1 eq, 2.6 mmol) are put in suspension in 10 ml of isopropanol and 14 ml of methanol and heated to 65° C. A solution of 365 mg of choline.Cl (1 eq, 2.6 mmol) in 1.5 ml of isopropanol is added and the yellow reaction medium is stirred for 30 minutes at 65° C. After return to ambient temperature, the fine suspension is filtered, washed with 2×1 ml of isopropanol and then concentrated dry. The precipitation/crystallisation tests on the yellow solid residue have not for the moment functioned.

After 5 days of drying at 45° C. under high vacuum (<10-2 mbar), 820 mg of bright yellow solid (Batch CP0686) is obtained. Traces of solvent (15% isopropanol) are detected by NMR.

The products are stored cool (2°–8° C.) and under inert gas in order to prevent any degradation. A complete analysis of the elafibranor salts is carried out, including identification and chemical purity.

Results:

The results are presented in FIG. 7 non-exhaustively:

Example 4: Solubility Test on Various Elafibranor Salts (GFT505)

This example presents the solubility characteristics of various forms and salts of elafibranor, with a view to parenteral administration or in the context of a quick-release enteral composition.

The solubilisation kinetics is determined in aqueous medium (water and pharmacopoeia buffers such as pH 7.4, 6.0 and 4.5 in particular), at ambient temperature. The results are indicated in tables 2 and 3.

TABLE 2

Different solubilities of elafibranor salts

| Products | Molecular weight | Melting point in ° C. | Solubility (according to Ph. Eur.) |
|---|---|---|---|
| Amorphous elafibranor | 384 | 144/145 | Very low solubility |
| Ethanolamine salt | 428 | — | Fairly soluble |
| Meglumine salt | 562 | — | Soluble |
| L-lysine salt | 513 | — | Very soluble |
| Tromethamine | 488 | — | Soluble |
| Choline salt | 487 | 197/199 | Very soluble |

TABLE 3

Solubility free basic elafibranor and choline salt in aqueous medium

| | Elafibranor (GFT505) choline salt | | Elafibranor (GFT505) Amorphous free basic | |
|---|---|---|---|---|
| Solvents | μM | mg/ml | μM | mg/ml |
| Buffer pH 4.6 | ND | ND | 114 | 0.044 |
| Buffer pH 7.4 | 82000 | 40 | 504 | 0.194 |
| Buffer pH 8.5 | ND | ND | 4419 | 1.701 |
| Propylene glycol | — | — | 33520 | 12.905 |
| Polyethylene glycol 400 | — | — | 39022 | 15.023 |

The choline salt for example has solubility at least 150 times greater than elafibranor in its free basic form.

Example 5: Dissolution Kinetics of Oral Formulations of Elafibranor Salts

The applicant studied the dissolution profile of several batches of capsules containing respectively choline salts and free basic elafibranor with an amorphous structure, in a unit dose equivalent to 120 mg in basic elafibranor form.

The dissolution tests were carried out on the majority of the formulations in media buffered to pH 6.0 USP and in gastric media simulating the nourished and fasting conditions, with the addition of enzymes (media called respectively FeSSIF and FaSSIF). The type II USP system with paddles was adopted for the tests with 1000 ml volume, 37° C., and the samples, taken at 0, 2, 5, 10, 15, 20, 30, 45 and 60 minutes, were analysed by HPLC without renewal of the media.

Results

The results show that elafibranor in the choline salt form is very quickly dissolved in the two FaSSIF and FeSSIF media. At the end of the test (60 minutes), 100% of the active substance is dissolved for the formulations and there is no difference according to the dissolution medium studied for the elafibranor choline salt, which is not the case with the formulations containing elafibranor in free basic form.

The dissolution kinetics is appreciably quicker for the formulations based on choline salt.

In conclusion, the impact of the elafibranor salt on the dissolution properties are surprising. The tests on the salt-based formulations have a similar profile whatever the medium simulating the taking or not of meals.

On the basis of these predictive in vitro data, it is therefore probable that the formulations based on choline salts have improved absorption related to greater solubility and quicker dissolution, making it possible to be free from any impact/variation related to the taking of food.

Example 6: Stability of Elafibranor and the Salts Thereof

The applicant decided to check the stability of elafibranor in free basic form and salt form after exposure to light and ambient temperature.

Experimental Protocol

Samples were prepared in the form of powder alone and aqueous solutions from the following samples: elafibranor, elafibranor choline.

Stability is measured over a period of 7 to 14 days by UPLC MS, with the calculation of the degree of recovery of the elafibranor peak with respect to the initial value and measurement of its purity index. The products are exposed to daylight and to ambient temperature.

As for the referenced samples, these were stored cool (2-8° C.), protected from light by aluminium paper and under inert gas for the solid product.

Results

Table 4 below shows, as an example, the qualitative photostability results of the choline salt (recovery in %) according to its physical state (solution or powder) after storage for two weeks.

TABLE 4

Photostability of elafibranor salts (recovery/theory)

| Products | Data T0 | Stability 14 days (solution) | Stability 14 days (powder) |
|---|---|---|---|
| Choline salt | 100 | >90% | ~90% |

They demonstrate that elafibranor in salt form, in particular choline, has a mean change of colouring under light (photosensitivity), yellow to medium yellow, whether in powder form or in solution, with less intensity than GT505 in its free basic form. Recovery after 14 days of storage is within the norm 100±10%.

The temperature had no impact on stability. The degradation products under light were not identified.

The invention claimed is:

1. A composition comprising as an active principle a pharmaceutically acceptable salt of elafibranor, wherein the pharmaceutically acceptable salt of elafibranor is the choline salt of elafibranor.

2. The composition according to claim 1, wherein the composition is in a form suitable for enteral administration.

3. The composition according to claim 1, wherein the composition is in a form suitable for parenteral administration.

4. The composition according to claim 3, wherein the composition is in a form suitable for intravenous administration.

5. The composition according to claim 3, wherein the elafibranor salt is micronised or has an amorphous structure.

6. The composition according to claim 3, wherein the elafibranor salt is in the form of a powder for a soluble injectable preparation.

7. The composition according to claim 1, wherein the composition is in a form suitable for subcutaneous administration.

8. The composition according to claim 1, comprising at least one excipient chosen from binders, disintegrating agents, diluents, lubricants, surfactants, buffers, flow agents, dyes, flavourings, sweeteners, solvents or preservatives.

9. The composition according to claim 1, comprising more than 50% particles with a size of less than or equal to 10 μm and all the particles with a size of less than 20 μm.

10. The composition according to claim 1, wherein the elafibranor salt has a dissolution profile in simulated FaSSIF and FeSSIF media greater than 90% after 30 minutes.

11. The composition according to claim 1, wherein the pharmaceutically acceptable salt of elafibranor (GFT505) is photostable.

12. The composition according to claim 1, wherein the composition is for treatment of liver diseases.

13. The composition according to claim 12, wherein the liver disease consists of non-alcoholic hepatic steatosis (NAFLD).

14. The composition according to claim 12, wherein the liver disease consists of non-alcoholic steatohepatitis (NASH).

15. The composition according to claim 12, wherein the liver disease consists of hepatic fibrosis.

16. The composition according to claim 12, wherein the liver disease consists of cirrhosis.

17. The composition according to claim 12, wherein the liver disease consists of hepatic autoimmune illnesses.

* * * * *